United States Patent
Thanner et al.

(10) Patent No.: US 7,053,533 B2
(45) Date of Patent: May 30, 2006

(54) PIEZOELECTRIC RESONATOR ELEMENT OF CYRSTALLOGRAPHIC POINT GROUP 32

(75) Inventors: Herbert Thanner, Graz (AT); Peter Krempl, Kainbach (AT)

(73) Assignee: Akubio Limited, Cambridge (GB)

( * ) Notice: Subject to any disclaimer, the term of this patent is extended or adjusted under 35 U.S.C. 154(b) by 0 days.

(21) Appl. No.: 10/478,854

(22) PCT Filed: May 28, 2002

(86) PCT No.: PCT/AT02/00160

§ 371 (c)(1),
(2), (4) Date: Mar. 5, 2004

(87) PCT Pub. No.: WO02/097984

PCT Pub. Date: Dec. 5, 2002

(65) Prior Publication Data

US 2004/0189153 A1    Sep. 30, 2004

(30) Foreign Application Priority Data

May 31, 2001 (AT) ................................ A 848/2001

(51) Int. Cl.
*H01L 41/08* (2006.01)
(52) U.S. Cl. ................. 310/361; 310/312; 310/321
(58) Field of Classification Search ................... None
See application file for complete search history.

(56) References Cited

U.S. PATENT DOCUMENTS

| | | | | |
|---|---|---|---|---|
| 4,234,812 A * | 11/1980 | Kawashima | ............. | 310/361 |
| 4,242,096 A * | 12/1980 | Oliveira et al. | ............. | 436/500 |
| 4,418,299 A * | 11/1983 | Momosaki | ............. | 310/361 |
| 4,735,906 A * | 4/1988 | Bastiaans | ............. | 436/527 |
| 5,001,053 A * | 3/1991 | Takahashi et al. | ............. | 435/7.1 |
| 5,221,873 A * | 6/1993 | Totty et al. | ............. | 310/361 |
| 5,705,399 A * | 1/1998 | Larue | ............. | 436/501 |
| 6,005,331 A * | 12/1999 | Sakharov et al. | ............. | 310/360 |
| 6,518,778 B1 * | 2/2003 | Vig et al. | ............. | 324/727 |
| 6,580,196 B1 * | 6/2003 | Shiono et al. | ............. | 310/313 A |
| 6,621,194 B1 * | 9/2003 | Sugimoto et al. | ............. | 310/368 |

OTHER PUBLICATIONS

P. Krempl et al., "Gallium Phosphate, GaPO$_4$: A New Piezoelectric Crystal Material for High-Temperature Sensories" in *Sensors and Actuators*, A61 (1997), pp. 361-363.

Nakazawa et al., "Reliable Quadratic for Frequency-Turnover Temperature VS Orientation of Rotated Y-Cut Quartz Plate Resonator Oscillating in C-Mode", 1994 IEEE International Frequency Control Symposium.

(Continued)

*Primary Examiner*—Mark Budd
(74) *Attorney, Agent, or Firm*—Morgan Lewis & Bockius LLP

(57) ABSTRACT

A piezoelectric resonator element of crystallographic point group 32, which can be operated as a thickness shear resonator contacting a carrier medium includes a singly rorated Y-cut (S1,S2) that is essentially rotated through an angle φ about the crystallographic x-axis, which differs from crystal cuts that are temperature-compensated in air or vacuum, wherein the cut has a negative temperatue coeffcient of the resonace frequency f(T) in a predetermined temperature range, preferably between 10° C. and 40° C., when there is no contact with the carrier medium, while the value of the linear temperature coeffcient a of resonance frequency in the same temperature range is less than 1 ppm/° C., preferably less than 0.5 ppm/° C. when the resonator is inb contact with the carrier medium. The resonator element (1) can additionally be provided with at least one layer sensitive to the parameter to be measured.

21 Claims, 2 Drawing Sheets

OTHER PUBLICATIONS

I. Postnikov, "Effect of Temperature or Frequency Characteristics of Contoured-Quartz Thickness-Shear-Type Vibrators" *Acoustical Physics*, 40 (1994), Jul./Aug., No. 4, pp. 586-592.

F. Eichelbaum et al., "Oszillatoren für Quartz-Crystal-Microbalance-Sensoren in Flüssigkeiten" in *Technisches Messen*, 65 (1998), pp. 434-444.

* cited by examiner

PIEZOELECTRIC RESONATOR ELEMENT OF CYRSTALLOGRAPHIC POINT GROUP 32

BACKGROUND OF THE INVENTION

The invention relates to a piezoelectric resonator element of crystallographic point group 32, which can be operated as a thickness shear resonator in contact with a carrier medium, and a measuring system for determining at least one chemical, biochemical or physical parameter in a carrier medium, which carrier medium can be brought into contact, on at least one side, with a piezoelectric resonator element of point group 32 having electrical contacts and —if required —at least one sensitive layer, where at least one resonance property, i.e., preferably the resonance frequency of the resonator element operated as a thickness shear resonator provides a measure for the chemical, biochemical or physical parameter to be determined.

Such resonator elements are employed for instance in micro-balances, which are based on the effect that the resonance properties of a piezoelectric resonator, usually a thickness shear resonator, are changed by the mass load on the resonator surface and by the viscosity or the electrical conductivity of the adjacent medium. Microbalances of this sort are frequently used for the in-situ measurement of layer thickness via the mass load. In these applications the microbalances are operated in vacuum. Recently this technique has also been used for determining the concentration of certain components in liquids or gases, where at least one surface of the resonator is provided with a selectively binding layer, which essentially binds only the substance to be measured to the resonator surface, thus increasing the oscillating mass.

Since the resonance properties of a piezoelectric resonator are not only dependent on the oscillating mass but also on capacitances which act in series with or parallel to the resonator, it is also possible to measure electrical properties such as conductivity or the dielectric constant, respectively changes in these properties, of liquids or gases.

A disadvantage of all these applications lies in the fact, that temperature changes in the resonator itself as well as in the medium to be measured may exert a considerable influence on the resonance properties, especially on the resonance frequency, which either necessitates the use of costly and cumbersome thermostatic devices to counter the effects of temperature fluctuations, or compels one to accept a reduced sensitivity and accuracy of the sensor. From the paper "Oszillatoren für Quartz-Crystal-Microbalance-Sensoren in Flüssigkeiten", Technisches Messen 65 (1998) by F. Eichelbaum, R. Borngräber, R. Lucklum, P. Hauptmann and S. Rösler, it is for instance known that the temperature dependence of the resonance frequency, i.e., the oscillator frequency of the predominantly used quartz AT-cut resonators, which is very low in air, especially at room temperature, shows a considerable slope of 35 Hz/° C. at a fundamental frequency of 10 MHz in the case of one-sided contact with water. Stated independently of the fundamental frequency this is 3.5 ppm/° C.

DESCRIPTION OF THE PRIOR ART

In U.S. Pat. No. 5,487,981 A for instance, the influence of temperature changes in a liquid on the resonance frequency of a quartz AT thickness shear resonator is measured using a resistance thermometer, and the corresponding offset frequency is computed by a programmable controller and electronically compensated. This of course is a relatively costly procedure.

The temperature dependence of the resonance frequency of a piezoelectric resonator may for instance be described by the following equation:

$$[f(T)-f(T_0)]/f(T_0)=a(T-T_0)+b(T-T_0)^2+c(T-T_0)^3$$

with
$f(T)$ resonance frequency at temperature T
$f(T_0)$ resonance frequency at reference temperature $T_0$
a,b,c linear, quadratic, cubic temperature coefficient The reference temperature $T_0$ may be freely chosen. In this patent description only the linear temperature coefficient a is used to describe the temperature dependence of the resonance frequency $f(T)$, which may for instance be determined by a linear fit over a predetermined temperature range, e.g., between 10° C. and 40° C. The quadratic and cubic coefficients are not taken into account.

SUMMARY OF THE INVENTION

It is the object of the present invention to propose a resonator for a measuring system for the determination of a chemical, biochemical or physical parameter in a carrier medium, which avoids the disadvantages mentioned above. Measurement sensitivity is to be preserved or even improved in the case of temperature fluctuations in the resonator or in the medium to be measured without the need for costly correcting devices.

According to the invention this object is achieved by proposing that the resonator element be a singly rotated Y-cut that is essentially rotated through an angle Φ about the crystallographic x-axis, which differs from crystal cuts that are temperature-compensated in air or vacuum, and that said cut have a negative temperature dependence of the resonance frequency f(T) in a predetermined temperature range, preferably between 10° C. and 40° C., when there is no contact with the carrier medium, while the value of the linear temperature coefficient a of the resonance frequency in the same temperature range is less than 1 ppm/° C., preferably less than 0.5 ppm/° C. when the resonator is in contact with the carrier medium.

Surprisingly it was found that a piezoelectric resonator, which in air, in a temperature range between 20° C. and 35° C., has a negative linear temperature coefficient a of the resonance frequency f(T)—with a value between 0.5 ppm/° C. and 3.5 ppm/° C., has an almost temperature-independent resonance frequency in this temperature range when in one-sided contact with distilled water.

The interaction between the oscillating surface of the resonator and the adjacent medium depends largely on the excited oscillation mode. In piezoelectric resonators longitudinal and transversal modes can be excited.

In the case of a longitudinal mode the direction of the displacement of the crystal surface is essentially normal to the resonator surface. In this case the resonators, especially when in contact with a fluid, show a strong dampening of the resonant oscillation, which leads to severe restriction of the measurement range and the resolution of such sensors.

Resonators which are excited in essentially transversal oscillation modes show a much better oscillation behavior especially when in contact with liquid media. The best known representatives of this class are so called thickness shear resonators, such as the quartz AT or BT cut.

The temperature dependence of the resonance frequency of a piezoelectric resonator is determined by the cut-direction of the resonator platelet relative to the crystallographic axes.

The signs of the cutting angles Φ indicating the rotation direction about the crystallographic axes, are given in accordance with the "IEEE Standard on Piezoelectricity"; ANSI/IEEE Std. 176-1987.

The quartz industry however still uses the standard from the year 1949, which will give the opposite sign for the cutting angle.

The following table will show the difference:

| Standard | Quartz AT (Φ[°]) | Quartz BT (Φ[°]) |
|---|---|---|
| 1949 | +35°15' *) | −48°50' *) |
| 1987 | −35°15' | +48°50' |

*) J.Zelenka: Piezoelectric Resonators and their Applications, Elsevier 1986

In the case of a preferably aqueous carrier medium with low viscosity (kinematic viscosity γ<15 mm$^2$s$^{-1}$ at 25° C.), which is in at least one-sided contact with the resonator, the invention proposes the following cutting angles Φ, depending on the application and material chosen for the resonator:

For quartz in the ranges:
−36.5°±1.1°, preferably −35.9°±0.5°
+52.5°±3.0°, preferably +51.4°±1.3°
For langasite in the range:
+6.3°±3.0°, preferably +5.3°±2.0°
For gallium orthophosphate in the range:
−21.2°±4.5°, preferably −18.5°±1.7°.

In a variant, where the resonator is in at least one-sided contact with a viscous carrier medium (kinematic viscosity γ>15 mm$^2$s$^{-1}$ at 25° C.), for instance oil, the following cutting angles Φ are proposed:

For quartz in the ranges:
−45.0°±7.0°, preferably −41.5°±3.5°
+60.0°±8.0°, preferably +60.0°±6.0°
For langasite in the range:
+30.0°±19.0°, preferably +22.0°±11.0°
For gallium orthophosphate in the range:
−35.0°+10.0°, preferably −40.0°±5.0°.

The advantages claimed for the resonator according to the invention will largely be maintained if it is ensured during manufacture of the resonator that a rotation about the z-axis preceding the rotation about the x-axis is kept small, values between −10° and +10°, preferably between −5° and +5°, being permissible.

BRIEF DESCRIPTION OF THE DRAWINGS

The invention will be further described below with reference to the enclosed drawings.

DETAILED DESCRIPTION

Figure 1:
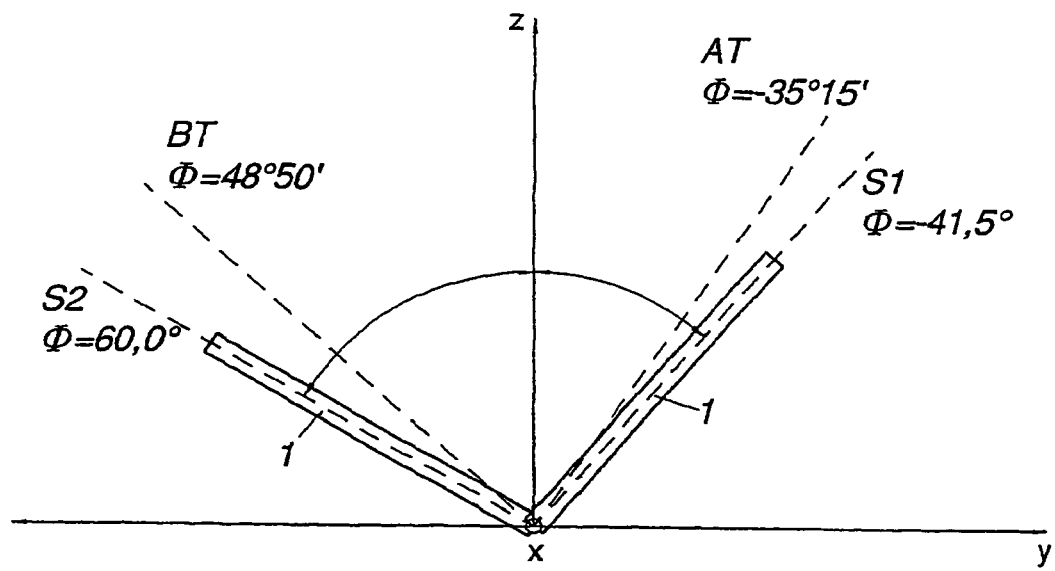
FIG. 1 shows a piezoelectric resonator element according to the invention.

In FIG. 1 the cutting angles ϕ for two quartz resonator elements 1 according to the invention — the two singly rotated Y-cuts S1 and S2 are shown in comparison with AT or BT cuts which are temperature-compensated in air or vacuum, the cuts S1 and S2 being optimized for viscous carrier media such as oil.

Figure 2:
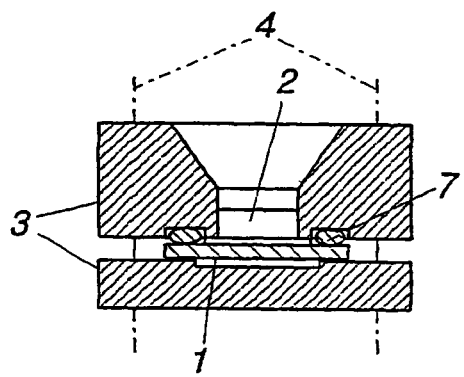
FIG. 2 shows a measurement system with a piezoelectric resonator element according to the invention in a sectional view.

FIG. 2 shows a two-part measurement cell 3 for liquids, whose parts are screw-connected at two points 4. In between there is a piezoelectric resonator element 1 with electrodes at the exterior surfaces, which is sealed against the upper part of the housing by an elastic sealing ring 7. The carrier medium, i.e. the liquid 2 to be measured, is in direct contact with the resonator surface which can be excited to oscillate piezo-electrically. To protect the resonator element 1 against aggressive carrier media it may be coated with a chemically inert protecting layer.

Figure 3:
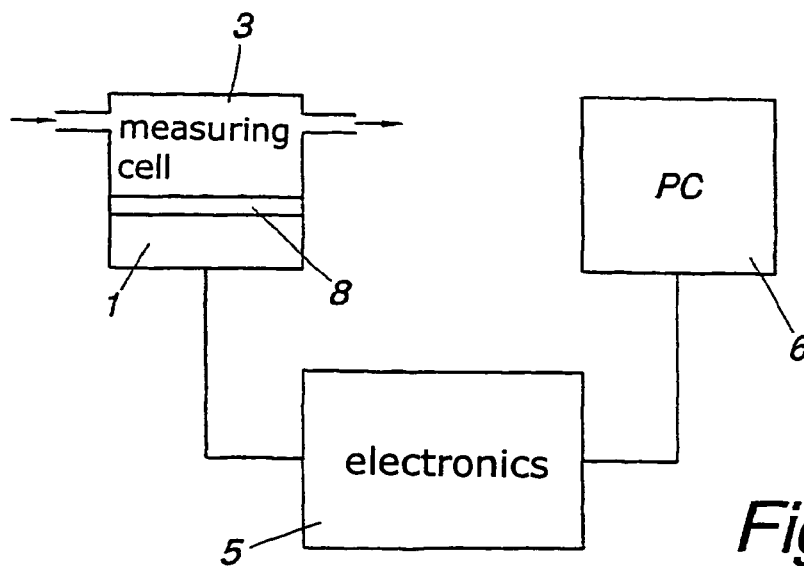
FIG. 3 is a schematic view of the measuring system.

FIG. 3 is a schematic drawing of a measuring system according to the invention. The piezoelectric resonator element 1 contained in the liquid measuring cell 3 is electrically connected with electronic measurement and evaluation units 5 and 6. The resonator surface may be coated with a layer 8 which is sensitive relative to at least one sample parameter.

Figure 4:
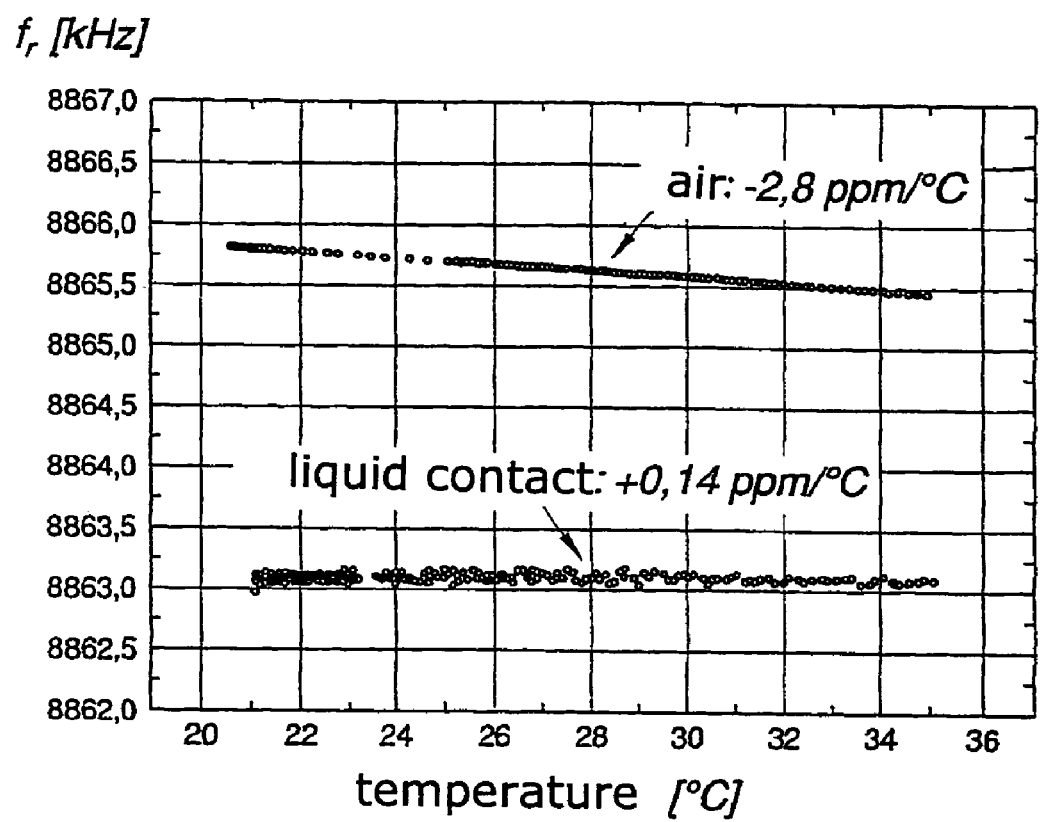
FIG. 4 shows the temperature dependence of the resonance frequency of the resonator element of FIG. 1 in air and in water.

FIG. 4 shows the measured temperature dependence of the resonance frequencies of a quartz thickness shear resonator (Φ=−35.6°), which is provided with gold electrodes on both sides, in air and in one-sided contact with distilled water, in the temperature range between 20° C. and 35° C. While the temperature dependence of the resonance frequency of the resonator oscillating in air shows a negative linear temperature coefficient a with a value of about 2.8 ppm/° C., the linear temperature coefficient a of the resonance frequency of the resonator in one-sided liquid contact is only about 0.14 ppm/° C., i.e. smaller by a factor 20.

What is claimed is:

1. Measuring apparatus for determining a chemical or physical property in a liquid carrier medium, or of the interaction of that substance with a selective binding layer, the apparatus comprising a piezoelectric resonator element of point group 32, the selective binding layer being attached to a surface of the element which, in use, is in contact with said liquid carrier medium, the piezoelectric resonator element having a resonance frequency, when operated as a thickness shear resonator, which provides a measure of the property or interaction to be determined, wherein the element is formed from a non AT cut of the crystal, said cut being a rotated Y-cut which is rotated through an angle ϕ about the crystallographic x-axis, wherein said cut has a negative temperature dependence of resonance frequency in a predetermined temperature range between 10° C. and 40° C. when there is no contact with said carrier medium, and wherein, when the resonator element is in contact with the carrier medium the element has a linear temperature coefficient of resonance frequency, in the temperature range, which is less than that of a pure AT cut under the same conditions.

2. The measuring apparatus of claim 1, wherein the temperature dependence in the carrier is less than 1 ppm/° C. when the resonator is in contact with the carrier medium.

3. Measuring apparatus according to claim 1, wherein said value of said linear temperature coefficient is less than 0.5 ppm/° C.

4. Measuring apparatus according to claim 1, wherein the apparatus is operable to analyze a substance in a carrier medium of low viscosity, and wherein the cutting angles ϕ are as follows:

for a quartz resonator element is in one of the ranges: −36.5°±1.1° C., and +52.5°±3.0°,
for a langasite element in the range +6.3 ±3.0° and
for a gallium orthophosphate element in the range: −21.2°±4.5°.

5. Measuring apparatus according to claim 1, wherein the apparatus is operable to analyze a substance in a carrier medium of low viscosity, and wherein the cutting angles φ are as follows:
for a quartz element in one of the ranges: −35.9°±0.5°, and 51.4°±1.3°,
for a langasite element in the range: 5.3°±2.0° and
for a gallium orthophosphate element in the range: −18.5°±1.7.

6. Measuring apparatus according to claim 5, wherein said carrier medium of low viscosity is an aqueous carrier medium.

7. Measuring apparatus according to claim 1, wherein the apparatus is operable to analyze a substance in a viscous carrier medium, and wherein the cutting angles φ are as follows:
for a quartz resonator element in one of the ranges: −45.0°±7.0, and +60.0°±8.0°,
for a langasite element in the range +30.0°±19.0° and
for a gallium orthophosphate element in the range: −35.0°±10.0°.

8. Measuring apparatus according to claim 1, wherein the apparatus is operable to analyze a substance in a viscous carrier medium, and wherein the cutting angles φ are as follows:
for a quartz resonator element in one of the ranges: −41.5°±3.5°, and +60.0°±6.0°,
for a langasite element in the range +22.0°±11.0° and
for a gallium orthophosphate element in the range: −40.0°±5.0°.

9. A measuring apparatus according to claim 1, wherein the rotation about the x-axis is preceded by a rotation about the z-axis by a non-zero angle between −10° and +10°.

10. A measuring apparatus according to claim 1, wherein the rotation about the x-axis is preceded by a rotation about the z-axis by a non-zero angle between −5° and +5°.

11. The measuring apparatus according to claim 7, wherein kinematic viscosity of the viscous carrier medium is greater than 15 mm$^2$s$^{-1}$ at 25° C.

12. The measuring apparatus according to claim 7, wherein kinematic viscosity of the viscous carrier medium is greater than 15 mm$^2$ s$^{-1}$ at 25° C.

13. The measuring apparatus according to claim 12, wherein the viscous carrier medium is oil.

14. The measuring apparatus according to claim 12, wherein the viscous carrier medium is oil.

15. A measuring system for determining at least one chemical, biochemical or physical parameter in a liquid carrier medium, the measuring system comprising said liquid carrier medium and a piezoelectric resonator element of point group 32 having electrical contacts, the element being in contact, on at least one side, with the carrier medium, said resonator element being arranged to operate as a thickness shear resonator when in contact with said liquid, the resonance frequency providing a measure for said chemical, biochemical or physical parameter to be determined, wherein said resonator element is a single rotated Y-cut which is essentially rotated through an angle φ about the crystallographic x-axis, said angle φ deviating from crystal cuts that are temperature-compensated in air or vacuum, and which has a negative temperature dependence of resonance frequency f(T) in a predetermined temperature range between 10° C. and 40° C., when there is no contact with said carrier medium, while the value of the linear temperature coefficient a of said resonance frequency in said predetermined temperature range is less than 1 ppm/° C. when said resonator is in contact with said carrier medium.

16. A system according to claim 15, wherein said piezoelectric resonator element has at least one sensitive layer.

17. A system according to claim 15, wherein said value of said linear temperature coefficient is less than 0.5 ppm/° C.

18. A method of making a piezoelectric crystal resonator element for a measuring apparatus for determining a chemical or physical property of a substance in a liquid carrier medium or of the interaction of that substance with a selective binding layer on the element, the method comprising the steps of:
(a) determining the temperature coefficient of resonance frequency in air or vacuum of a number of rotated Y-cuts of the crystal rotated about the x-axis by different angles, over a predetermined temperature range;
(b) determining a negative linear temperature coefficient, over said temperature range in air or a vacuum, of a cut of crystal which, is such that the linear temperature coefficient of the resonance frequency of the crystal when in contact with the liquid carrier medium of a lower magnitude than that of a pure AT-cut crystal; and
(c) selecting, using the data obtained in step (a) above, a crystal having a cut angle which gives a temperature coefficient in air or a vacuum which satisfies step (b).

19. A method according to claim 18, in which said negative linear temperature coefficient is determined by measuring the linear coefficient of resonant frequency, over said temperature range, of an AT-cut crystal in contact with the liquid and reversing the sign of the measured coefficient.

20. A method according to claim 18, in which the temperature range is between 10° C. and 40° C.

21. A method according to claim 18 in which the method comprises the further step (d) of applying a selective binding layer to the selected crystal.

* * * * *